United States Patent [19]

Lee

[11] Patent Number: 5,677,461

[45] Date of Patent: Oct. 14, 1997

[54] METHOD FOR PRODUCING CHROMIUM PICOLINATE COMPLEX

[75] Inventor: Myoung Hee Lee, Changwon, Rep. of Korea

[73] Assignee: Republic of Korea Represented by Rural Development Administration, Suwon, Rep. of Korea

[21] Appl. No.: 629,386

[22] Filed: Apr. 8, 1996

[30] Foreign Application Priority Data

Apr. 13, 1995 [KR] Rep. of Korea ............... 1995-8651

[51] Int. Cl.⁶ .................................................. C07D 213/22
[52] U.S. Cl. ............................................................ 546/263
[58] Field of Search ....................................... 546/263, 327

[56] References Cited

U.S. PATENT DOCUMENTS 4,315,927  2/1982  Evans ........................................ 424/245

OTHER PUBLICATIONS

Evans et al., Composition and Biological Activity of Chromium–Pyridine Carboxylate complexes, J. Inorg. Biochem., 49, pp. 177–187, (1973).

*Primary Examiner*—Mukund J. Shah
*Assistant Examiner*—Deepak R. Rao
*Attorney, Agent, or Firm*—Foley and Lardner

[57] ABSTRACT

A method for producing chromium picolinate complex by the reaction of picolinic acid with chromium, wherein the reaction is carried out under the conditions of temperature of 70° C. and pH of 3.5 to 4.2.

6 Claims, No Drawings

METHOD FOR PRODUCING CHROMIUM PICOLINATE COMPLEX

BACKGROUND OF THE INVENTION

1. Field of the Invention

The present invention relates to a method for producing chromium picolinate complex with high availability in the living bodies. More particularly, the present invention relates to a new method for producing chromium picolinate complex characterized by that the reaction temperature and pH of the reaction solution are controlled to promote the reaction, by which not only the reaction time is extremely reduced but also the yield of the product gets higher than 95%.

2. Description of the Prior Art

Chromium, one of the transition elements, belongs to the 4th period of the periodic table and exists in $Cr^{+3}$ or $Cr^{+6}$ state in the living bodies depending on its oxidation state. $Cr^{+3}$ have been extensively studied for its nutritive-physiological functions, while $Cr^{+6}$ is known as a poisonous material which shows strong toxicity with a very small quantity, and no physiological function thereof has been found. It was found that $Cr^{+3}$ is an essential factor for the carbohydrates metabolism in mice, and thereafter, it was found that $Cr^{+3}$ is a constituent of GTF(Glucose Tolerance Factor) which maximizes the functions of insulin in the living bodies, so that it should be administered through food or feed as an essential trace element. Further, it was reported that a long-term chromium deficiency leads to shortening of lifetime as well as suppression of growth.

According to the research reports up to now, the most important function of chromium is that it acts as a supplementary factor helping insulin combined to its receptors perform its functions at cell membranes. Accordingly, under chromium deficiency, the level of sugar in the blood cannot be properly controlled in spite of a sufficient level of insulin, resulting in intolerance to sugar and high blood sugar level. It was reported that the typical intolerance to sugar observed from the old ages can be normalized by the administration of GTF or chromium inorganic salts contained in the yeast extracts.

Chromium is involved in the metabolism of not only carbohydrates but also fats and proteins, because it maximizes the functions of insulin. It was also reported that, for a mouse with cholesteraemia induced by feed containing sugar as a main energy source, the administration of water containing chromium can significantly reduce the cholesterol level in the blood.

Since the amino acid transport and protein synthesis are promoted by insulin, chromium deficiency may lead to the reduction of intake of glycine, serine, methionine and β-amino-butyric acid by the muscular cells. Accordingly, in order to facilitate the metabolism of the living bodies, the administration of a proper amount of chromium as an essential trace metal is necessarily requested.

According to the Recommended Dietary Allowance of F. D. A., it is recommended that an adult should ingest 50~200 μg of chromium daily. However, since the intake of chromium from diet has been greatly reduced due to the increasing chances to take the processed and refined foods, 90% of the population is ingesting 50 μg or less chromium in a day, which does not come up to the minimum recommended daily dosage. Moreover, they prefer to take pure starches such as sugar exceedingly. Besides, since there exists no mechanism to maintain the homeostasis of chromium in the blood in the living bodies, the excess chromium in the blood due to the intake of excess carbohydrates is excreted through urines. Accordingly, the excretion of chromium may be promoted by the intake of excess refined carbohydrate food, in addition to various diseases, stress due to the environmental factors and pregnancy. Although newborn babies have an adequate amount of endogenous chromium in the internal organs and tissues, the concentrations of chromium in all the organs and tissues are continuously reduced as they get older. The deficiency of chromium is a wide-spread phenomenon and, a research report in the U. S. A. reported that the excess excretion of chromium due to various factors, which cannot be compensated by dietary intake of chromium, leads to a significant reduction of chromium level in the tissues of the middle aged and the old aged. This problem of human nutrition is also identically applied to the nutrition of animals.

Internal absorption and availability of dietary chromium highly depend on the chemical states of chromium. Although chromium itself has no biochemical function, it becomes physiologically active in the living bodies, when complexed with the organic compounds. Since the conventional chromium supplements in the form of inorganic salts of chromium, yeast extracts or nicotinic acid-chromium complexes are absorbed poorly in the digestive tracts, such malabsorption leads to chromium deficiency in the living bodies. The absorption of inorganic salts of chromium to the digestive tracts is known to be about 0.05~3%, which is extremely lower than that of organo chromium compounds. The absorption of chromium ions into the small intestine is inhibited by competing metals such as zinc, copper, manganese and vanadium, etc.

Although chromium contained in the animal foods, which exists in the state of complexes with organic compounds, is absorbed more easily than the inorganic chromium, it has a problem that its content is extremely low. Further, a very small amount of organic chromium contained in the vegetable foods exists in the sate which hardly can be utilized in the living bodies.

As a solution to these problems, the administration of chromium in the form of chromium picolinate complex was suggested, and said complex has a character that cannot be decomposed easily in the digestive organs of animals because it is very stable. Therefore, when said complex is administered with diet, its absorption is not inhibited by other competing metal ions or other ingredients of food, so that its internal absorption is very high.

In the mean time, picolinic acid is known to be a metabolite of amino acids, produced from tryptophan in the liver, kidney and pancreas of animals, and also known to be a physiological carrier for zinc, copper and chromium ions during their transport from the small intestine to the blood. Further, picolinic acid is a structural isomer of nicotinic acid which is one of the constituents of GTF derived from yeast.

U.S. Pat. No. 4,315,927 to Evans discloses a method for producing chromium picolinate complex comprising the step of dissolving 5.12 g of $CrCl_3 \cdot 6H_2O$ and 7.5 g of picolinic acid in 40 ml water, the step of allowing said reaction solution to stand at room temperature for 24 hours to obtain the precipitates, and the step of filtering and drying said precipitates to obtain the final product. However, said method has problems that quite a long reaction time is required and yield of chromium picolinate complex is very low.

Under these circumstances, the present inventors made extensive studies to provide a new method for producing chromium picolinate complex wherein the desired complex can be easily produced with higher yields, and they found that said object can be accomplished by adjusting the temperature and pH of the reaction to the specific ranges.

SUMMARY OF THE INVENTION

Therefore, an object of the present invention is to provide a method for producing chromium picolinate complex by the reaction of picolinic acid with chromium, characterized by that said reaction is carried out under the condition of the temperature range of 40°~90° C. and pH range of 4.2 or less.

Other objects, features and applications of the present invention shall be apparent to the skilled in the art from the following detailed description of the invention.

DETAILED DESCRIPTION OF THE INVENTION

The present invention will be described in more detail hereinafter.

The feature of the present invention is that the reaction of picolinic acid with chromium is carried out in the specific temperature and pH ranges, and thereby, the reaction time is greatly reduced and the yield of the desired product is significantly improved. All the conventional reactions of picolinic acid with chromium were carried out at room temperature, and the reaction at the temperature of 40°~90° C. according to the present invention has never been suggested nor taught.

According to the U.S. Pat. No. 4,315,927, the metal picolinate complex is produced by the reactions of picolinic acid with various metals, wherein said reactions are carried out at room temperature for 24 hours and the obtained complexes are purified by recrystallization using hot water or under boiling.

However, according to the method of the present invention, the reaction time is significantly reduced, as well as the yield of the product is greatly improved. Further, the desired complex can be obtained without the step of recrystallization.

Chromium used in the present invention is in the form of $Cr^{+3}$, or its salts, and its chlorides such as $CrCl_3$ or $CrCl_3 \cdot 6H_2O$ are preferably used by dissolving them in 5~10 times weight of water. The molar ratio of picolinic acid to chromium is at least about 3:1, and the reaction of picolinic acid with chromium is carried out under the condition of pH of 4.2 or less, preferably pH of 3~4 and more preferably pH of 3.5~4. The reaction temperature of the present invention is in the range of 40°~90° C., but the room temperature may be adapted. When the reaction is carried out at room temperature, it is necessary to allow the reaction solution to stand for several hours. On the other hand, if the reaction is carried out at the temperature of 40°~90° C., the reaction time is in the range of 10~40 minutes, preferably 10~30 minutes. When the precipitation of complex is completed, the reaction mixture is cooled, filtered by vacuum suction, washed with water and then dried to obtain the chromium picolinate complex.

According to the present invention, by carrying out the reaction under the condition of the temperature of 40°~90° C. for 10~40 minutes, the yield of the product can be improved up to 40~50%, greatly higher than the yield of 18% in the method of the U.S. Pat. No. 4,315,927. Further, according to the present invention, the yield of 40~50% also can be attained by adjusting the pH of the reaction solution to 4.2 or less and allowing the solution to stand at room temperature for several hours. At this time, the pH of the reaction solution must be carefully adjusted so as not to go over 4.2. When the pH of the reaction solution is over 4.2, olation is initiated to form a physiologically inactive polynucleate complex, which cannot be absorbed into the digestive organs.

In order to promote the reaction, the pH is preferably adjusted to 3~4.2, and more preferably to 3.5~4. Further, according to the present invention, the period of reaction time can be significantly reduced to 10~30 minutes and the yield of the product can be highly improved to 95~98% by adjusting the pH of the reaction solution to 3.5~4 and, at the same time, heating the solution to the temperature of 40°~90° C. to prevent the olation and to promote the substitution of water molecules coordinated to chromium with picolinic acid.

Thus obtained chromium picolinate complex can be administered in order to prevent or alleviate chromium deficiency in the form of additives for foods or feed, tablets or capsules. Further, said chromium picolinate complex in combination with essential inorganic materials such as Ca, K, Na, Mg, Fe, Mn, Cu, Zn, Se and I, and water-soluble or fat-soluble vitamins can be administered in the form of tablets or capsules. Administration of chromium picolinate complex maximizes the functions of insulin in the living bodies to promote the metabolism of carbohydrates, proteins and fats, so that the levels of sugar and cholesterol in the blood can be normalized. Further, the level of proteins in the bodies can be increased, while the level of fats can be reduced. Moreover, the weight of livestock can be increased and the efficiency of feed can be improved significantly.

The following examples are intended only to further illustrate the invention and are not intended to limit the scope of the invention which is defined by the claims.

COMPARATIVE EXAMPLE 1

5.12 g of $CrCl_3 \cdot 6H_2O$ (chloride of $Cr^{+3}$) and 7.5 g of picolinic acid were dissolved in 40 ml water. Thereafter, the reaction mixture was allowed to stand at room temperature for 24 hours. The resulting precipitates were filtered, washed with water and then dried to obtain 1.5 g of chromium picolinate complex(yield: 18.9%).

COMPARATIVE EXAMPLE 2

5.12 g of $CrCl_3 \cdot 6H_2O$ (chloride of $Cr^{+3}$) and 7.1 g of picolinic acid were dissolved in 30 ml water. Thereafter, the reaction mixture was heated at 40° C. for 30 minutes with stirring. When the precipitation was completed, the reaction mixture was cooled, filtered by vacuum suction, washed with water and then dried to obtain 4.18 g of chromium picolinate complex(yield: 52.6%).

EXAMPLE 1

5.12 g of $CrCl_3 \cdot 6H_2O$ and 7.1 g of picolinic acid were dissolved in 30 ml of water. The pH of the reaction mixture was adjusted to 3.8 by the addition of 4N NaOH solution and the mixture was allowed to stand at room temperature for 2 hours. Thereafter, the mixture was filtered by vacuum suction, washed and then dried to obtain 4.5 g of chromium picolinate complex(yield: 56.0%).

EXAMPLE 2

5.12 g of $CrCl_3 \cdot 6H_2O$ and 7.1 g of picolinic acid were dissolved in 30 ml of water and pH of the reaction mixture was adjusted to 3. Thereafter, the reaction mixture was heated at 90° C. for 10 minutes, cooled, filtered by vacuum suction, washed and then dried to obtain 6 g of chromium picolinate complex(yield: 74.6%).

EXAMPLE 3

5.12 g of $CrCl_3 \cdot 6H_2O$ and 7.1 g of picolinic acid were dissolved in 30 ml of water and pH of the reaction mixture was adjusted to 3.5. Thereafter, the reaction mixture was heated at 80° C. for 10 minutes, cooled, filtered by vacuum suction, washed and then dried to obtain 7.3 g of chromium picolinate complex(yield: 90.8%).

EXAMPLE 4

5.12 g of $CrCl_3 \cdot 6H_2O$ and 7.1 g of picolinic acid were dissolved in 30 ml of water and pH of the reaction mixture was adjusted to 3.8. Thereafter, the reaction mixture was heated at 70° C. for 10 minutes, cooled, filtered by vacuum suction, washed and then dried to obtain 7.8 g of chromium picolinate complex(yield: 97.0%).

COMPARATIVE EXAMPLE 3

5.12 g of $CrCl_3 \cdot 6H_2O$ and 7.1 g of picolinic acid were dissolved in 30 ml of water and pH of the reaction mixture was adjusted to 4.7. Thereafter, the mixture was allowed to stand at room temperature for 1 hour, filtered by vacuum suction, washed and then dried. Thus obtained chromium picolinate complex was forming a polynucleate complex, the product of olation.

EXPERIMENTAL EXAMPLE 1

Eight mice were divided into two groups of four animals each. To the mice in the first group, 150 ng of $^{51}Cr$ in the form of $CrCl_3$, a conventional inorganic chromium compound used for the dministration of chromium, was administered orally by using tubes. To the mice in the second group, 150 ng of $^{51}Cr$ in the form of chromium picolinate complex produced by the method of the present invention was administered orally by using tubes. In order to compare the internal absorption of the two compounds, the livers and kidneys were extracted from all the mice 120 hours after the administration of the compounds. The amount of radiation in 1.0 g of each extracted sample was measured and the results are shown in Table 1.

TABLE 1

| Chromium Compound | Radiation Amount(cpm) | |
|---|---|---|
| | Liver | Kidney |
| $CrCl_3$ | 287 ± 54 | 360 ± 35 |
| Chromium Picolinate Complex | 1055 ± 150 | 1475 ± 25 |

As shown in Table 1, the levels of chromium in the livers and the kidneys of the chromium picolinate complex-administered group were 3.8 times and 4.0 times higher respectively than those of the $CrCl_3$-administered group. This indicates that the absorption of chromium in the form of chromium picolinate complex is at least 4 times higher than that in the form of $CrCl_3$.

EXPERIMENTAL EXAMPLE 2

5 nM of $(4,5-^3H)L$-leucine or 5 nM of $(6-^3H)D$-glucose was added to a cell culture solution containing 1.0 μM chromium in the form of $CrCl_3$ or chromium picolinate complex produced by the method of the present invention. Muscular cells of mice were cultivated in the culture solution at 37° C. for 1 hour. The cultivated cells were filtered and then washed to measure the radiation amounts thereof. The results are shown in Table 2.

TABLE 2

| Chromium Compound | Radiation Amount(cpm) | |
|---|---|---|
| | $(6-^3H)D$-glucose | $(4,5-^3H)L$-leucine |
| $CrCl_3$ | 465 ± 34 | 172 ± 11 |
| Chromium Picolinate Complex | 634 ± 56 | 327 ± 49 |

As can be seen in Table 2, in case that the chromium picolinate complex was added to the culture solution, 1.8 times of glucose and 3 times of L-leucine were absorbed into the muscular cells and utilized in the biosynthesis, when compared with the case that $CrCl_3$ was added to the culture solution.

EXPERIMENTAL EXAMPLE 3

Eight pigs were divided into two groups of four animals each. Chromium picolinate complex produced by the method of the present invention was added to the feed for pig breeding so that the concentration thereof might be 200 ppb, and the feed was administered to the pigs of the first group from 35 days to 56 days after their birth. To the second group as a control, conventional feed containing no chromium picolinate complex was administered. The weight increase per day and the feed efficiency of both groups were measured. The results are shown in Table 3.

TABLE 3

| | Control | Chromium Picolinate Complex-administered group |
|---|---|---|
| Weight increase per day(g) | 420 | 467 |
| Feed Consumption(g) | 819 | 789 |
| Feed Efficiency* | 1.95 | 1.69 |

(Note) Feed Efficiency = Feed Consumption/Weight increase per day

As can be seen in Table 3, the weight increase per day and the feed efficiency were greatly improved by the addition of chromium picolinate complex.

What is claimed is:

1. A method for producing a chromium picolinate complex by a reaction of picolinic acid with chromium, wherein said method comprises reacting picolinic acid with a $Cr^{+3}$ salt under the conditions of a temperature of from 70° to 90° C., and a pH of from 3.5 to 4.2.

2. The method according to claim 1, wherein the reaction is carried out under the conditions of a temperature of from 70° to 90° C., and a pH of from 3.5 to 4.0 for a reaction time of from 10 to 30 minutes.

3. The method according to claim 1, wherein the molar ratio of picolinic acid to chromium is at least about 3:1.

4. The method according to claim 1, wherein the $Cr^{+3}$ salt is a chloride selected from the group consisting of $CrCl_3$ and $CrCl_3 \cdot 6H_2O$.

5. The method according to claim 4, wherein said chloride is dissolved in 5 to 10 times its weight of water.

6. The method according to claim 2, wherein said reaction has a yield of said chromium picolinate complex of from 95% to 98%.

* * * * *